United States Patent
Muroyama et al.

(10) Patent No.: US 8,114,658 B2
(45) Date of Patent: Feb. 14, 2012

(54) METHOD OF MOISTURIZING SKIN

(75) Inventors: Koutarou Muroyama, Nishinomiya (JP); Tatsuya Ohara, Kakogawa (JP); Yoshitaka Hirose, Itami (JP); Norio Yamamoto, Kobe (JP); Shinji Murosaki, Nara (JP); Yoshihiro Yamamoto, Itami (JP)

(73) Assignee: House Wellness Foods Corporation, Hyogo (JP)

( * ) Notice: Subject to any disclaimer, the term of this patent is extended or adjusted under 35 U.S.C. 154(b) by 363 days.

(21) Appl. No.: 12/310,068

(22) PCT Filed: Aug. 10, 2006

(86) PCT No.: PCT/JP2006/315868
§ 371 (c)(1),
(2), (4) Date: May 28, 2009

(87) PCT Pub. No.: WO2008/018143
PCT Pub. Date: Feb. 14, 2008

(65) Prior Publication Data
US 2009/0324563 A1 Dec. 31, 2009

(51) Int. Cl.
*C12N 1/20* (2006.01)

(52) U.S. Cl. .................... 435/252.9; 424/93.45

(58) Field of Classification Search .................. None
See application file for complete search history.

(56) References Cited

U.S. PATENT DOCUMENTS

| | | |
|---|---|---|
| 7,510,734 B2 * | 3/2009 | Sullivan et al. ............ 424/780 |
| 2005/0196480 A1 | 9/2005 | Sullivan et al. |
| 2005/0272694 A1 | 12/2005 | Moriya et al. |

FOREIGN PATENT DOCUMENTS

| | | |
|---|---|---|
| JP | 4-264034 | 9/1992 |
| JP | 4-356409 | 12/1992 |
| JP | 5-017363 | 1/1993 |
| JP | 2001-139412 | 5/2001 |
| JP | 2002-145737 | 5/2002 |
| JP | 2006-76903 | 3/2006 |
| WO | 2004/078188 | 9/2004 |
| WO | 2004/084922 | 10/2004 |
| WO | 2004/084923 | 10/2004 |
| WO | 2006/000992 | 1/2006 |

OTHER PUBLICATIONS

International Search Report issued Sep. 5, 2006 in the International (PCT) Application of which the present application is the U.S. National Stage.
Supplementary European Search Report dated Sep. 14, 2009 in Application No. EP 06 78 2654.
S. Murosaki et al., "Heat-killed *Lactobacillus plantarum* L-137 suppresses naturally fed antigen-specific IgE production by stimulation of IL-12 production in mice", Journal of Allergy and Clinical Immunology, Mosby—Year Book, Inc., US, vol. 102, No. 1, pp. 57-64, Jul. 1, 1998.
S. Murosaki et al., "Effects of Intake of Syrup Supplemented with Nigerooligasaccharides and Heat-killed *Lactobacillus plantarum* L-137 on Skin Symptom and Immune Function in Patients with Atopic Dermatitis", Japanese Pharmacology & Therapeutics, vol. 34, No. 10, pp. 1087-1096, 2006, English Abstract.

* cited by examiner

*Primary Examiner* — Kade Ariani
(74) *Attorney, Agent, or Firm* — Wenderoth, Lind & Ponack, L.L.P.

(57) ABSTRACT

The present invention provides a moisturizer comprising heat-killed cells of *Lactobacillus plantarum* as an active ingredient. The moisturizer of the present invention improves the water retention capacity of the stratum corneum, and is useful for prevention and improvement of rough skin.

4 Claims, 1 Drawing Sheet

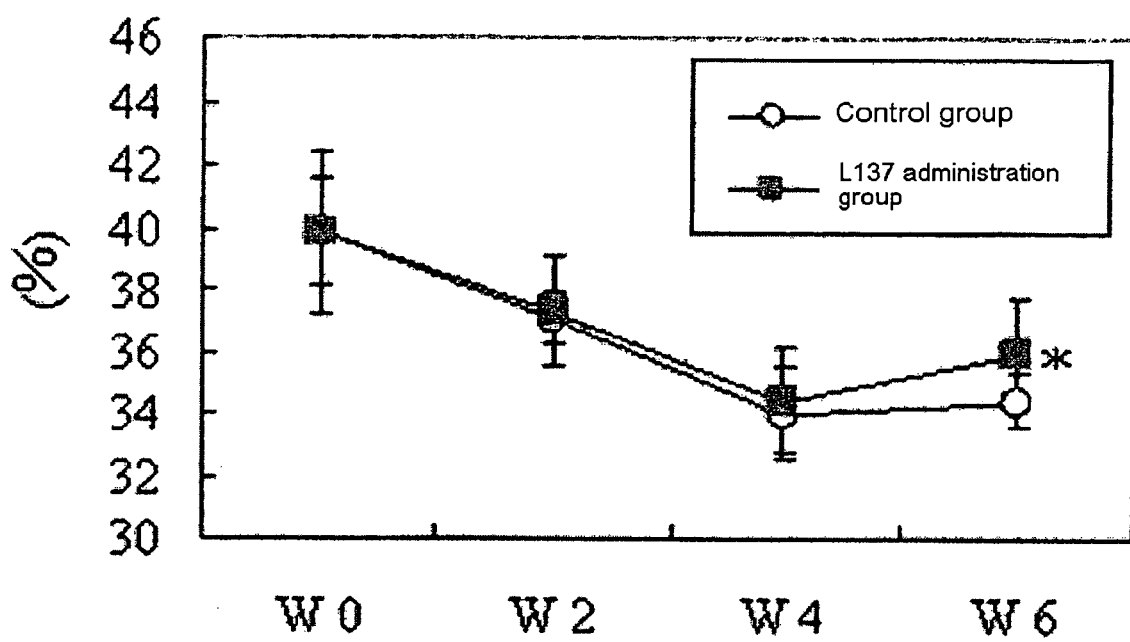

METHOD OF MOISTURIZING SKIN

This application is a U.S. national stage of International Application No. PCT/JP2006/315868 filed Aug. 10, 2006.

TECHNICAL FIELD

The present invention relates to a moisturizer, in more detail, a moisturizer comprising heat-killed cells of *Lactobacillus plantarum*.

BACKGROUND ART

Human skin is covered with the stratum corneum, which is a thin biological protective membrane. This stratum corneum exposed to the external world allows us to live in the dry atmosphere without losing water. The stratum corneum is thin and supple, and contributes to maintenance of healthy skin by preventing loss of body water. Healthy skin is generally said to have a water content of 10 to 20%.

However, aging, change of seasons, etc. may impair normal system for controlling the water content in the stratum corneum, causing rough skin or serious skin problems. Conventionally, an external moisturizer containing polyhydric alcohols such as glycerol, hyaluronic acid, chondroitin, collagen, a mucopolysaccharide, etc. for improving the water retention capacity of the stratum corneum and preventing rough skin has been known (see JP-A No. 2001-89381, JP-A No. 2002-145753 and JP-A No. 2005-314402). Also, an external moisturizer containing β-glucan and heat-treated cells of *Enterococcus faecalis* in combination has been known (see JP-A No. 2004-269408). In addition, a beauty food containing ceramide and viable cells of *lactobacillus* in combination has been known (see JP-A No. 2004-254632).

DISCLOSURE OF THE INVENTION

Problem to be Solved by the Invention

In view of the situation, an object of the present invention is to provide a moisturizer which has a beneficial moisturizing effect. In particular, an object of the present invention is to provide a moisturizer which exhibits a moisturizing effect by oral administration (internal use).

Means for Solving the Problem

In order to solve the above-described problem, the present inventors conducted intensive investigations and found that orally-administered heat-killed cells of *Lactobacillus plantarum* exhibit a beneficial moisturizing effect. They have carried out further investigations based on the finding, and completed the present invention.

Namely, the present invention relates to:
(1) a moisturizer comprising heat-killed cells of *Lactobacillus plantarum* as an active ingredient;
(2) the moisturizer according to the above (1), wherein the *Lactobacillus plantarum* is *Lactobacillus plantarum* L-137 (FERM BP-08607);
(3) the moisturizer according to the above (1) or (2), which is for oral administration;
(4) a method for moisturizing skin, comprising administering an effective dose of heat-killed cells of *Lactobacillus plantarum* to a human who needs moisturization of skin; and
(5) a use of heat-killed cells of *Lactobacillus plantarum* for producing a moisturizer.

EFFECT OF THE INVENTION

The moisturizer of the present invention exerts a beneficial moisturizing effect in prevention or improvement of various cutaneous symptoms including wrinkles, sagging, tensioned skin, speckles and dullness, when administered orally, or applied directly to skin.

BRIEF DESCRIPTION OF DRAWINGS

FIG. 1 shows the temporal change of the water content in the stratum corneum (%) of the control group and the administration group of the heat-killed cells of *Lactobacillus plantarum* L-137 (simply shown as L137 administration group in the figure) in Test Example 1.

BEST MODE FOR CARRYING OUT THE INVENTION

The active ingredient of the moisturizer of the present invention is heat-killed cells of *Lactobacillus plantarum*, which are obtained by heat treatment of *Lactobacillus plantarum*. Exemplary bacteria of *Lactobacillus plantarum* include *Lactobacillus plantarum* L-137, *Lactobacillus plantarum* JCM 1149 type strain, *Lactobacillus plantarum* L-051 (Fermentation Research Institute Microorganism No. 11912) etc., and inter alia *Lactobacillus plantarum* L-137 is the most preferred. The above-mentioned *Lactobacillus plantarum* L-137 is deposited as FERM BP-08607 (transferred from FERM P-15317 deposited on Nov. 30, 1995) at International Patent Organism Depositary, National Institute of Advanced Industrial Science and Technology.

The above-mentioned bacteria used in the present invention can be obtained by culture on various culture media, such as a natural medium, a synthetic medium, and a semisynthetic medium. The culture medium contains a nitrogen source and a carbon source. The nitrogen source may be, for example, a meat extract, peptone, gluten, casein, a yeast extract, an amino acid, etc., and the carbon source may be, for example, glucose, xylose, fructose, inositol, maltose, starch syrup, koji extract, starch, bagasse, wheat bran, molasses, glycerol, etc. In addition, minerals such as ammonium sulfate, potassium phosphate, magnesium chloride, sodium chloride, iron, manganese and molybdenum; vitamins; etc. may be added. The culture temperature may be about 25 to 40° C., preferably about 27 to 35° C., and the culture duration may be about 12 to 48 hours, optionally with aerated shaking. The pH of the culture medium may be about 3 to 6, preferably about 4 to 6.

After culture, heat-killed cells may be prepared as follows: cells are collected first from the medium, and then the collected cells are heat-treated; or cells are heat-treated in the medium before isolation, and then the heat-killed cells are collected. The method for cell collection may be, for example, a method in which distilled water is added to the culture medium, supernatant is removed by centrifugation etc., the above-described operation is repeated if needed, and then cells are collected by centrifugation, filtration, etc.

The heat-killed cells of *Lactobacillus plantarum* of the present invention can be obtained by subjecting collected viable cells or the entire culture medium containing viable cells to heating treatment for inactivation, followed by drying in a suitable way such as spray drying and freeze drying. The heating temperature is usually about 60 to 100° C., preferably about 70 to 90° C. The heating means may be a known means using a heater. The heating duration is usually about 5 to 40 minutes, preferably about 10 to 30 minutes after the desired temperature is attained.

In oral administration of the moisturizer of the present invention, a daily dose of the heat-killed cells as an active ingredient may be about 0.4 mg to 2 g, preferably about 1 mg to 1 g, more preferably about 5 mg to 0.5 g for an adult weighing about 60 kg although it depends on the sex, age, weight and conditions (symptoms) of the subjects to be administered. When directly applied to skin, a preferable daily dose of the heat-killed cells as an active ingredient is usually about 0.01 to 2.5 mg, preferably about 0.02 to 1 mg per 10 cm$^2$ of the application site although it may be suitably selected depending on the skin area to be treated. The above daily dose to be administered may be administered or applied in a single dose or divided multiple doses.

In oral administration (internal use), the moisturizer of the present invention may be a solid pharmaceutical preparation, such as powder, a granule, a pill, a tablet and a capsule, or a liquid such as a syrup. In the production of these pharmaceutical preparations, a carrier or additive suitable for the formulation can be used. Examples of the carrier or additive include an excipient (sodium polyacrylate, calcium polyacrylate, carboxymethylcellulose, lactose, dextrin, cornstarch, crystalline cellulose, saccharose, sodium chloride, glucose, urea, starch, calcium carbonate, kaolin, silicic acid, potassium phosphate, etc.), a lubricant (magnesium stearate, sucrose fatty acid ester, glycerine fatty acid ester, purified talc, polyethylene glycol, etc.), a disintegrant (calcium carboxymethylcellulose, anhydrous dibasic calcium phosphate, sodium carboxymethylcellulose, low substituted hydroxypropylcellulose, dry starch, sodium alginate, agar powder, sodium hydrogencarbonate, calcium carbonate, etc.), a binder (hydroxypropylcellulose, liquid gum arabic, water, ethanol, propanol, simple syrup, dextrose in water, starch in water, gelatin in water, carboxymethylcellulose, methylcellulose, polyvinyl pyrrolidone, etc.), a solubilizer (gum arabic, polysorbate 80, etc.), an absorption enhancer (sodium lauryl sulfate etc.), a buffering agent (phosphate buffer solution, acetate buffer solution, borate buffer solution, carbonate buffer solution, citrate buffer solution, tris buffer solution, etc.), a preservative (methyl parahydroxybenzoate, ethyl parahydroxybenzoate, propyl parahydroxybenzoate, butyl parahydroxybenzoate, chlorobutanol, benzyl alcohol, benzalkonium chloride, sodium dehydroacetate, disodium edetate, etc.), a thickener (propylene glycol, glycerol, hydroxyethyl cellulose, hydroxypropyl cellulose, polyvinyl alcohol, polyethylene glycol, etc.), a stabilizer (sodium hydrogensulfite, sodium thiosulfate, sodium edetate, sodium citrate, ascorbic acid, dibutyl hydroxytoluene, etc.), or a pH adjustor (hydrochloric acid, sodium hydroxide, phosphoric acid, acetic acid, etc.).

The moisturizer of the present invention may also be contained in cosmetics. Examples of the cosmetics include cleansing preparations such as body wash, hand wash and face wash; skin-care preparations such as lotion, milky lotion and cream; make-up preparations such as foundation, under makeup base and face powder; etc. The amount of the blended moisturizer of the present invention in the cosmetics is not particularly limited, but usually, the preferable amount of heat-killed cells of *Lactobacillus plantarum* as an active ingredient is 0.01 to 2.5% (W/W) and more preferably 0.02 to 1% (W/W) to the total amount of the cosmetics.

EXAMPLE

Hereinafter, the present invention will be illustrated by Test Examples and Examples, but it is not limited thereto.

Test Example 1

*Lactobacillus plantarum* L-137 (FERM BP-08607) was inoculated into 6 L of a culture medium containing 1% glucose, 1% yeast extract, 0.5% poly peptone, 0.2% meat extract, 0.2% sodium acetate, 0.001% manganese sulfate tetrahydrate, 0.001% iron sulfate heptahydrate, 0.001% sodium chloride and 0.05% sucrose fatty acid ester, and cultured at 32° C. for 24 hours. After culture, cells were collected by centrifugation of the culture medium at 5000 rpm for 35 minutes. The obtained cells were dispersed in saline, centrifugation at 5000 rpm for 35 minutes was performed, and then supernatant was removed for cell collection. After 3-time repetition of this operation, cells were dispersed in ion-exchanged water, heated at 70° C. for 10 minutes, and then freeze-dried to yield about 7 g of heat-killed cells. The heat-killed cells were added to a powder feed product (CE-2 made by CLEA Japan, Inc.) so that the heat-killed cells accounted for 0.01% by weight as a final concentration, and mixed.

For 1 week of preliminary rearing before the start of the test, 7-week-old hairless mice (HR-1, female, supplied by Japan SLC, Inc.) were fed with CE-2 powder feed and water ad libitum. The mice were grouped based on body weight (8 mice in each group). One group was fed with the above-prepared feed containing heat-killed cells of *Lactobacillus plantarum* L-137, and the other group, as a control group, was fed with CE-2 powder feed not containing heat-killed cells of *Lactobacillus plantarum* L-137 for 6 weeks.

Every 2 weeks after the grouping, the skin on the right side and the left side in the area from the center of the back to the lower body (from lower back to buttocks) were alternately measured 5 times each (10 times in total) with a skin moisture analyzer (Moisture Checker MY-808S made by Scalar Corp.). After exclusion of 2 highest values and 2 lowest values, the mean of the other 6 values was determined as the water content in the stratum corneum (%) of the individual. The mean±SD (standard deviation) of each group was calculated from the above-obtained water contents in the stratum corneum of individuals in the group. FIG. 1 shows the temporal change thereof.

FIG. 1 clearly shows that there was no difference between the heat-killed cells of *Lactobacillus plantarum* L-137 administration group and the control group until Week 4, but that the water content in the stratum corneum of the administration group was significantly improved at Week 6 in comparison with that of the control group.

Example 1

The ingredients were well mixed in the amounts described in the following Table 1, and the mixture was compressed into tablets each weighing 500 mg and containing 10 mg of the moisturizer of the present invention.

TABLE 1

| Ingredient | Amount (% by weight) |
| --- | --- |
| Heat-killed cells prepared in Test Example 1 | 2 |
| Lactose | 93 |
| Crystalline cellulose | 1 |
| Talc | 4 |

Example 2

A cream preparation containing the ingredients in the following Table 2 in each predetermined amount was produced in the usual manner.

TABLE 2

| Ingredient | Amount (% by weight) |
| --- | --- |
| Heat-killed cells prepared in Test Example 1 | 0.2 |
| Polyethylene glycol | 2 |
| Self-emulsifying glyceryl monostearate | 5 |
| Cetyl alcohol | 4 |
| Squalane | 6 |
| Triglyceryl 2-ethylhexanoate | 6 |
| 1,3-butylene glycol | 7 |
| L-histidine | 3 |
| Purified water | q.s. to 100 |

Industrial Applicability

The present invention provides a moisturizer which improves the water retention capacity of the stratum corneum and is useful for prevention and improvement of rough skin.

The invention claimed is:

1. A method for moisturizing skin, comprising orally administering as active ingredient an effective dose of heat-killed cells of *Lactobacillus plantarum* to a human who needs moisturization of skin.

2. The method according to claim 1, wherein the *Lactobacillus plantarum* is *Lactobacillus plantarum* L-137 (FERM BP-08607).

3. The method according to claim 1, wherein the cells of *Lactobacillus plantarum* L-137 (FERM BP-08607) killed at about 70 to 90° C. are used.

4. The method according to claim 1, wherein the heat-killed cells of *Lactobacillus plantarum* L-137 (FERM BP-08607) are orally administered at a daily dose of about 1 mg to 1 g for an adult weighing about 60 kg.

* * * * *